(12) United States Patent
Dijkstra et al.

(10) Patent No.: US 11,648,415 B2
(45) Date of Patent: May 16, 2023

(54) THERAPEUTIC DEVICE FOR HUMAN HAIR AND SKINCARE

(71) Applicant: LIGHT TREE, Amstelveen (NL)

(72) Inventors: Alain Dijkstra, Amstelveen (NL); Yvonne Johanna Margaretha Houthuijs, Amstelveen (NL)

(*) Notice: Subject to any disclaimer, the term of this patent is extended or adjusted under 35 U.S.C. 154(b) by 413 days.

(21) Appl. No.: 16/996,933

(22) Filed: Aug. 19, 2020

(65) Prior Publication Data

US 2021/0101018 A1 Apr. 8, 2021

(30) Foreign Application Priority Data

Oct. 2, 2019 (IN) .............................. 201911039862

(51) Int. Cl.
*A61N 5/00* (2006.01)
*A61N 5/06* (2006.01)
(Continued)

(52) U.S. Cl.
CPC ........... *A61N 5/0617* (2013.01); *A61H 23/02* (2013.01); *A61K 35/16* (2013.01); *A61M 35/003* (2013.01); *A61H 2201/0153* (2013.01); *A61H 2201/105* (2013.01); *A61H 2201/501* (2013.01); *A61H 2201/5064* (2013.01); *A61H 2205/021* (2013.01); *A61M 2202/0423* (2013.01);
(Continued)

(58) Field of Classification Search
CPC .......... A61N 5/0617; A61N 2005/0644; A61N 2005/0652; A61N 2005/0659; A61M 35/003; A61M 2210/06; A61H 2201/0153; A61H 2201/105; A61H 7/002–005; A61H 7/006; A61H 15/02; A61H 35/008; A46B 13/04–08; A46B 15/0002; A46B 15/0004; A46B 15/0034; A46B 15/0036; A46B 2200/102; A46B 2200/104; A45D 24/10
See application file for complete search history.

(56) References Cited

U.S. PATENT DOCUMENTS 8,083,696 B2 12/2011 Vandenbelt et al.
2007/0149900 A1* 6/2007 Lin ........................ A61H 7/006
601/136
(Continued)

OTHER PUBLICATIONS

Madnani N, Khan K. Hair cosmetics. Indian J Dermatol Venereol Leprol 2013;79:654-67.

*Primary Examiner* — Philip R Wiest
*Assistant Examiner* — Sarah B Lederer
(74) *Attorney, Agent, or Firm* — Willie Jacques; Emanus, LLC

(57) ABSTRACT

A therapeutic device, for human hair and skincare, comprises a gripping unit a functional unit including a first functional module and a second functional module, the first functional module including a first plate and a second functional module including a second plate, wherein a second surface of the second plate is oriented in an opposite direction to a first surface of the first plate, a plurality of teeth oriented in the direction of the orientation of the first surface, the plurality of teeth including a plurality of respective primary Light Emitting Diodes (LEDs), a plurality of secondary LEDs provided on the second plate and oriented in the direction of the orientation of the second surface and a sensor unit configured to determine hair distribution data on a body portion of a user.

12 Claims, 10 Drawing Sheets

(51) Int. Cl.
*A61K 35/16* (2015.01)
*A61M 35/00* (2006.01)
*A61H 23/02* (2006.01)

(52) U.S. Cl.
CPC .. *A61M 2210/06* (2013.01); *A61N 2005/0626* (2013.01); *A61N 2005/0644* (2013.01); *A61N 2005/0652* (2013.01); *A61N 2005/0659* (2013.01); *A61N 2005/0663* (2013.01)

(56) References Cited

U.S. PATENT DOCUMENTS

2017/0348544 A1* 12/2017 Beerwerth ............ A61B 18/203
2018/0027942 A1* 2/2018 Jeon ........................ A46B 9/005
2019/0209077 A1* 7/2019 Charraud ............. A61B 5/0077

\* cited by examiner

THERAPEUTIC DEVICE FOR HUMAN HAIR AND SKINCARE

TECHNICAL FIELD

The present invention relates generally to therapeutic devices. Particularly and not exclusively, the present invention relates to a therapeutic device that is capable of providing massage therapy and skin treatment with the use of electromagnetic non-ionizing radiations.

BACKGROUND ART

The hair on a human scalp and other body organs are strings made up of dead keratin cells. The protein keratin is produced in hair follicles in the outer layer of human skin. As follicles produce new hair cells, old cells are being pushed out through the surface of the skin, causing hair growth over the skin. An average adult head has about 100,000 to 150,000 hairs. It is normal for an individual to lose 50~100 hairs a day which usually goes unnoticed.

The hair loss in human beings is classified into a plurality of categories including (i) involutional alopecia which is a natural condition in which the hair gradually thins with age, (ii) androgenic alopecia which is a genetic condition characterized by a receding hairline and gradual disappearance of hair from the crown and frontal scalp, (iii) alopecia areata which starts suddenly causing patchy hair loss in children and young adults, (iv) alopecia universalis which causes the fall out of all body hair including the hairs in eyebrows, eyelashes, and pubic hair, (v) telogen effluvium which refers to temporary hair thinning over the scalp due to changes in the growth cycle of hair including the side effect of medications, and (vi) scarring alopecias which results in the permanent loss of hair. Also, the absence of certain nutrients, as well as excess or oversupply can affect the hair growth cycle. The stress caused due to physical or emotional trauma can cause hair fall, hair shedding, and hair thinning. Further, medical conditions and medications for hypothyroidism and hyperthyroidism, high blood pressure, and chemotherapy in the treatment of certain types of cancer also cause hair loss. Furthermore, hair care practices and styling resulting in the scalp damage and unnecessary pressure on hair follicles leading to hair breakage and loss.

Curative procedures for hair loss include cosmetic and surgical treatments and medications. While medication is safe to use for the treatment of hair loss, it comes with several potential side effects including mild irritation of the scalp, skin rashes, swollen lymph nodes, dryness of the skin and growth of hair on some undesirable location on the body, especially the sides of the face and hands. Further, the side effects of the medications for hair loss include decreased sexual drive and temporary impotence in men, cataracts, high blood sugar, and feminization of a male fetus during pregnancy.

Alternately, surgical procedures for stopping hair loss include hair transplant surgery, scalp reduction, and tissue expansion. The hair transplant surgery involves moving a small plug of skin with few hairs to the bald portion of the scalp. However, the drawback of hair transplant surgery as a treatment for hair loss is the requirement of multiple surgeries over time. In the scalp reduction process, a part of the scalp lacking hair is surgically removed and the area is closed with a piece of scalp having hair. In tissue expansion, two consecutive steps are followed. In the first step, a tissue expander is placed under a part of the scalp that has hair and that is present next to the bald spot. After several weeks, the tissue expander stretches out the part of the scalp that has hair. In the second step, the tissue expander is removed and the expanded area of the scalp with hair over the bald spot is pulled out. However, these surgical remedies are expensive and carry with them several risks including scars, infection, and bleeding.

As an alternative to the aforementioned medications and surgical procedures/treatment methods, low-level laser therapy (LLLT) is used for the prevention and reversal of hair loss. It is a form of light/heat treatment which is a safer procedure for the treatment of hair loss. The procedure uses a device that emits light which penetrates the scalp and causes the increased blood flow in the scalp resulting in the stimulation of hair follicles. Although the laser hair therapy is a non-invasive and painless procedure, the associated drawbacks include longer treatment time, high cost, ineffective for people in the advanced stages of hair loss, interaction with photosensitive medication, and non-establishment of long-term safety and long term effectiveness.

Moreover, in the interest of overall mental and physical health, it has further been observed that the massaging of the human body provides a moment of relaxation with reduced muscle tension and relief from chronic pain. The body massaging helps an individual to enhance his/her overall sense of emotional and physical well-being. The body massaging again is known to provide several benefits including, but not limited to, skin regeneration, relaxation of the nervous system, mobilization of the joints and places beneficial tension on the muscles, ligaments, and tendons of the body, filtering out dead cells, waste products, and possible pathogens from the body thereby causing the detoxification of the lymphatic system of the body, boosting the skeletal system thereby causing the increased blood flow with essential minerals to the bones. Also, the body massage effectuates vasodilation thereby causing the increased blood flow and enhanced delivery of oxygen to all organs of the body.

Also, body massage stimulates peristalsis facilitating the movement of food to different processing stations in the digestive tract of the human body. The body massage effectuates improved breathing. However, the traditional way of having a body massage by an expert masseur or massage therapist comes with a plurality of drawbacks. First and foremost, the skill sets of an individual masseur or massage therapist are subjective and may not equally beneficial to all groups of people. Besides receiving massage therapy from a human masseur also introduces risks of human errors that may cause more damage than good. Also, with the present global economic climate, people may be in short of time to avail of the benefits of good body massage.

Therefore there is a requirement in the art for a mechanized device capable of providing benefits of safe hair growth stimulation, skin therapy, and body massage that does not suffer from the aforementioned deficiencies.

OBJECTS OF THE INVENTION

Some of the objects of the present invention are as stated below:

It is an object of the present invention to provide a reliable light-based therapeutic device configured in the form of a hair comb for the treatment of hair loss and stimulation of hair growth and massage therapy;

It is another object of the present invention to provide a non-invasive light-based therapeutic device configured in the form of a hair comb for the treatment of hair loss and stimulation of hair growth and massage therapy;

It is yet another object of the present invention to provide a light-based therapeutic device with reduced side effects and configured in the form of a hair comb for the treatment of hair loss and stimulation of hair growth and massage therapy;

It is yet another object of the present invention to provide a cost-effective light-based therapeutic device configured in the form of a hair comb for the treatment of hair loss and stimulation of hair growth and massage therapy;

It is a further object of the present invention to provide a light-based therapeutic device with easy operability and a light-based therapeutic device configured in the form of a hair comb for the treatment of hair loss and stimulation of hair growth and massage therapy;

It is an additional object of the present invention to provide a light-based therapeutic device configured in the form of a hair comb for effective treatment irrespective of gender and age for the treatment of hair loss and stimulation of hair growth and massage therapy;

It is another object of the present invention to provide a light-based therapeutic device exhibiting long-term safety for the treatment of hair loss and stimulation of hair growth and massage therapy; and It is yet another object of the present invention to provide a light-based therapeutic device with reduced treatment time for the treatment of hair loss and stimulation of hair growth and massage therapy.

Other objects, aspects, features, and goals of the present invention will be better understood from the following detailed description.

SUMMARY

According to a first aspect of the present invention, there is provided a therapeutic device for human hair and skincare, the therapeutic device comprising a gripping unit, a functional unit including a first functional module and a second functional module, the first functional module including a first plate and a second functional module including a second plate, wherein a second surface of the second plate is oriented in an opposite direction to a first surface of the first plate, a plurality of teeth oriented in the direction of the orientation of the first surface, the plurality of teeth including a plurality of respective primary Light Emitting Diodes (LEDs), a plurality of secondary LEDs provided on the second plate and oriented in the direction of the orientation of the second surface and a sensor unit configured to determine hair distribution data on a body portion of a user.

In one embodiment of the invention, emission characteristics of the plurality of primary LEDs and the plurality of secondary LEDs are reconfigurable.

In one embodiment of the invention, the plurality of primary LEDs and the plurality of secondary LEDs are configured to emit electromagnetic radiation in red frequency ranges, infrared frequency ranges, and combinations thereof.

In one embodiment of the invention, diameters of the plurality of secondary LEDs are greater than diameters of the plurality of primary LEDs.

In one embodiment of the invention, the functional unit further includes a reservoir adapted to store a serum, and a plurality of fluid channels connecting the reservoir with the plurality of respective teeth, the plurality of teeth being adapted to dispense the serum.

In one embodiment of the invention, the therapeutic device further comprises a vibration motor configured to generate vibrations with predetermined vibration characteristics, the vibration motor being located between the first plate and the second plate.

In one embodiment of the invention, the therapeutic device further comprises an intermediary plate located between the first plate and the second plate, wherein the vibration motor is installed with the intermediary plate.

In one embodiment of the invention, the therapeutic device further comprises a control unit, the control unit including a processor, a memory unit and a communication unit, the memory unit including machine-readable instructions that when executed by the processor, enable the processor to receive a control input, via the communication unit, from an external electronic communication device, receive the hair distribution data from the sensor unit and modify emission characteristics of one or both of the plurality of primary LEDs and the plurality of secondary LEDs, in correlation with one or both of the control input and the hair distribution data.

In one embodiment of the invention, the functional unit further comprises an intermediary plate located between the first plate and the second plate, wherein the first plate includes a plurality of first openings, the plurality of teeth being installed onto the intermediary plate and being adapted to protrude through the plurality of first openings.

In one embodiment of the invention, each tooth of the plurality of teeth includes an elastic member attached with the intermediary plate, a primary tube attached with the elastic member, the primary tube including a respective primary LED of the plurality of primary LEDs, a secondary tube coaxially provided with respect to the primary tube and having an internal diameter that is larger than an external diameter of the primary tube, the secondary tube being fixed to one or both of a respective first opening of the plurality of first openings, and the intermediary plate.

In one embodiment of the invention, compression of the primary tube against the elastic member is configured to activate the respective primary LED.

In one embodiment of the invention, the plurality of primary LEDs are provided within the plurality of respective teeth and the plurality of secondary LEDs are provided on the second surface through Chip-on-Board (CoB) technology.

According to a second aspect of the present invention, there is provided a therapeutic device for human hair and skincare, the therapeutic device comprising a gripping unit, a functional unit including a first functional module and a second functional module, the first functional module including a first plate and a second functional module including a second plate, wherein a second surface of the second plate is oriented in an opposite direction to a first surface of the first plate, an intermediary plate located between the first plate and the second plate, a vibration motor configured to generate vibrations with predetermined vibration characteristics, a plurality of teeth oriented in the direction of the orientation of the first surface, the plurality of teeth including a plurality of respective primary Light Emitting Diodes (LEDs), a plurality of secondary LEDs provided on the second plate and oriented in the direction of the orientation of the second surface and a sensor unit adapted to determine hair distribution data on a body portion of a user.

In one embodiment of the invention, the first plate includes a plurality of first openings, the plurality of teeth being installed onto the intermediary plate and being adapted to protrude through the plurality of first openings.

In one embodiment of the invention, each tooth of the plurality of teeth includes an elastic member attached with the intermediary plate, a primary tube attached with the elastic member, the primary tube including a respective primary LED of the plurality of primary LEDs, a secondary tube coaxially provided with respect to the primary tube and having an internal diameter that is larger than an external diameter of the primary tube, the secondary tube being fixed to one or both of a respective first opening of the plurality of first openings and the intermediary plate.

In one embodiment of the invention, the therapeutic device further comprises a control unit, the control unit including a processor, a memory unit and a communication unit, the memory unit including machine-readable instructions that when executed by the processor, enable the processor to receive a control input, via the communication unit, from an external electronic communication device, receive the hair distribution data from the sensor unit, modify emission characteristics of the plurality of primary LEDs and the plurality of secondary LEDs, in correlation with one or both of the control input and the hair distribution data and activate the vibration motor in correlation with the control input.

According to a third aspect of the present invention, there is provided a method of utilizing a therapeutic device for human hair and skincare, the therapeutic device comprising a gripping unit, a functional unit including a first functional module and a second functional module, the first functional module including a first plate and a second functional module including a second plate, wherein an external surface of the second plate is oriented in an opposite direction to an external surface of the first plate, an intermediary plate located between the first plate and the second plate, a vibration motor configured to generate vibrations with predetermined vibration characteristics, a plurality of teeth oriented in the direction of the orientation of the external surface of the first plate, the plurality of teeth including a plurality of respective primary Light Emitting Diodes (LEDs), a plurality of secondary LEDs provided on the second plate and oriented in the direction of the orientation of the external surface of the second plate and a sensor unit adapted to determine hair distribution data on a body portion of a user. The method comprises steps of receiving a control input from an external electronic communication device, receiving the hair distribution data from the sensor unit and performing one or both of, modifying emission characteristics of one of the plurality of primary LEDs and the plurality of secondary LEDs, in correlation with one or both of the control input and the hair distribution data, and activating the vibration motor in correlation with the control input, in case the control input is indicative of the plurality of secondary LEDs.

BRIEF DESCRIPTION OF ACCOMPANYING DRAWINGS

So that the manner in which the above-recited features of the present invention can be understood in detail, a more particular description of the invention, briefly summarized above, may have been referred by embodiments, some of which are illustrated in the appended drawings. It is to be noted, however, that the appended drawings illustrate only typical embodiments of this invention and are therefore not to be considered limiting of its scope, for the invention may admit to other equally effective embodiments.

These and other features, benefits, and advantages of the present invention will become apparent by reference to the following text figure, with like reference numbers referring to like structures across the views, wherein.

DETAILED DESCRIPTION

Figure 1:
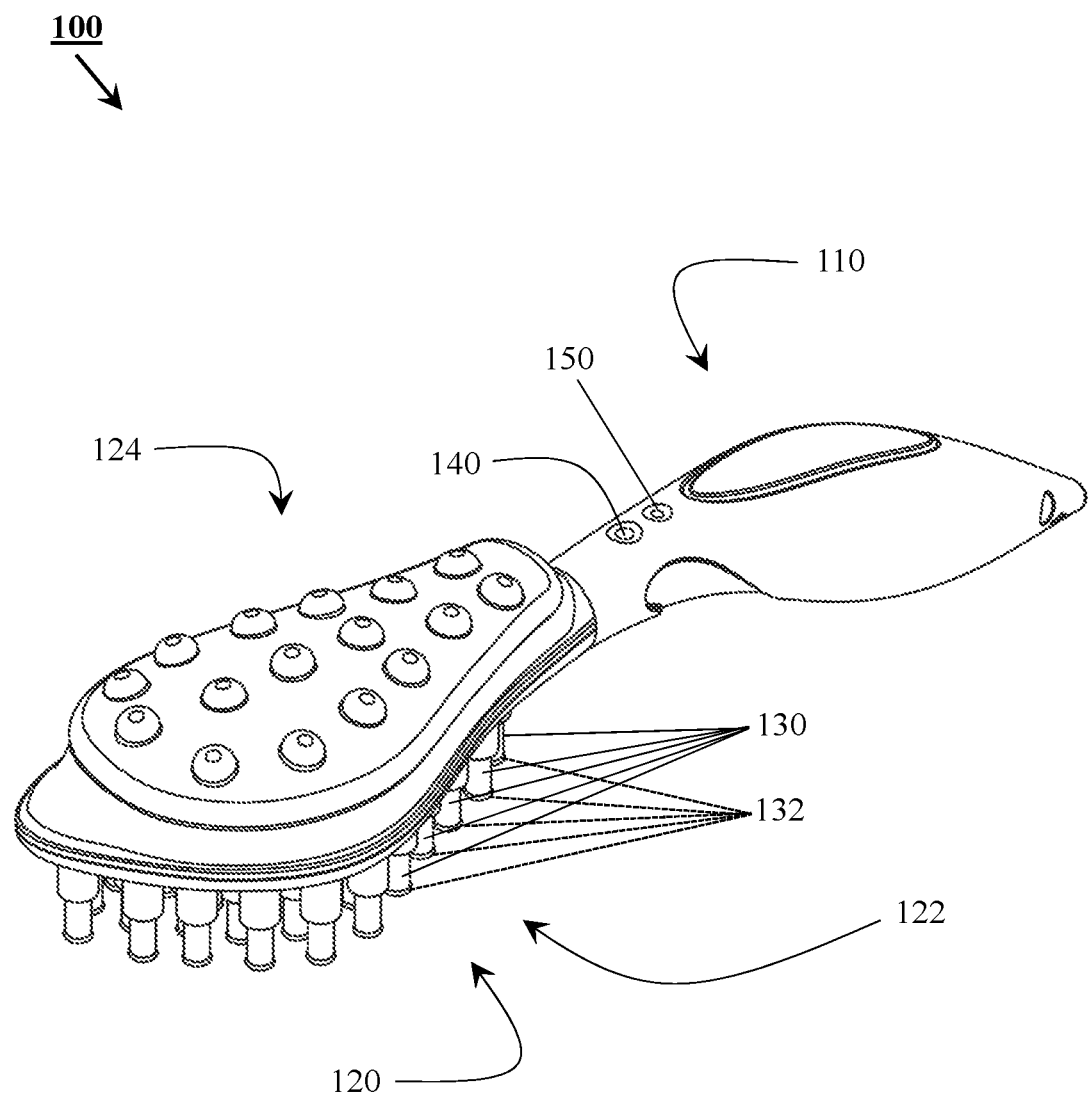
FIG. 1 illustrates an isometric view of a therapeutic device for human hair and skincare, in accordance with an embodiment of the present invention.

While the present invention is described herein by way of example using embodiments and illustrative drawings, those skilled in the art will recognize that the invention is not limited to the embodiments of drawing or drawings described, and are not intended to represent the scale of the various components. Further, some components that may form a part of the invention may not be illustrated in certain figures, for ease of illustration, and such omissions do not limit the embodiments outlined in any way. It should be understood that the drawings and detailed description thereto are not intended to limit the invention to the particular form disclosed, but on the contrary, the invention is to cover all modifications, equivalents, and alternatives falling within the scope of the present invention as defined by the appended claims. As used throughout this description, the word "may" is used in a permissive sense (i.e. meaning having the potential to), rather than the mandatory sense, (i.e. meaning must). Further, the words "a" or "an" mean "at least one" and the word "plurality" means "one or more" unless otherwise mentioned.

Furthermore, the terminology and phraseology used herein is solely used for descriptive purposes and should not be construed as limiting in scope. Language such as "including," "comprising," "having," "containing," or "involving," and variations thereof, is intended to be broad and encompass the subject matter listed thereafter, equivalents, and additional subject matter not recited, and is not intended to exclude other additives, components, integers or steps. Likewise, the term "comprising" is considered synonymous with the terms "including" or "containing" for applicable legal purposes. Any discussion of documents acts, materials, devices, articles, and the like is included in the specification solely to provide a context for the present invention. It is not suggested or represented that any or all of these matters form part of the prior art base or were common general knowledge in the field relevant to the present invention. In this disclosure, whenever a composition or an element or a group of elements is preceded with the transitional phrase "comprising", it is understood that we also contemplate the same composition, element or group of elements with transitional phrases "consisting of, "consisting", "selected from the group of consisting of, "including", or "is" preceding the recitation of the composition, element or group of elements and vice versa.

The present invention is described hereinafter by various embodiments with reference to the accompanying drawings, wherein reference numerals used in the accompanying drawing correspond to the like elements throughout the description. This invention may, however, be embodied in many different forms and should not be construed as limited to the embodiment set forth herein. Rather, the embodiment is provided so that this disclosure will be thorough and complete and will fully convey the scope of the invention to those skilled in the art. In the following detailed description, numeric values and ranges are provided for various aspects of the implementations described. These values and ranges are to be treated as examples only and are not intended to limit the scope of the claims. In addition, a number of materials are identified as suitable for various facets of the implementations. These materials are to be treated as exemplary and are not intended to limit the scope of the invention.

It is envisaged here that a therapeutic device be provided that is capable of providing light and massage therapy to hair and scalp, as well as other parts of a body of a user. Since the therapeutic device is intended to be used with relative convenience, it has been constructed as a handheld device that includes a gripping unit for firmly gripping the device and a functional unit that delivers the therapy. The therapy has been achieved through two independent modules provided on two opposite sides of the functional unit. A first module is constructed as a comb with telescopic teeth provided with primary Light Emitting Diodes (LEDs). Also, the telescopic teeth are capable of dispensing a serum to enhance hair growth and repair and to enable general care of the hair of the user. A second module has been provided with secondary LEDs that are also capable of providing light therapy to the scalp or other parts of the body of the user. Also, a vibration motor may be included, that may be capable of generating vibrations of predetermined characteristics to enhance the massaging and therapeutic effect of the second module.

FIG. 1 illustrates an isometric view of a therapeutic device 100 for human hair and skincare, in accordance with an embodiment of the present invention. The therapeutic device 100 includes a gripping unit 110 and a functional unit 120. The gripping unit 110 is supposed to act as a handle and is adapted to allow a user to be able to grip the therapeutic device 100, during use. In that regard, the gripping unit may be ergonomically shaped to comfortably and snugly comply with the palms of the user. Additionally, rubber-based grips may be installed onto the gripping unit 110, to provide sufficient friction between the gripping unit 110 and the palms of the user. The functional unit 120 includes a first functional module 122 and a second functional module 124. Also illustrated in FIG. 1 are a plurality of teeth 130 included within the first functional module 122.

Since the therapeutic device 100 is designed to be used on human hair, the plurality of teeth 130 will allow the first functional module 122 to act as a comb. The plurality of teeth 130, in turn, include a plurality of respective primary Light Emitting Diodes (LEDs) 132, preferably provided at ends of the plurality of teeth 130, that would be coming in contact with human hair during use of the therapeutic device 100. There is provided a switch 140 and a communication port 150 preferably in the gripping unit 110 of the therapeutic device 100. The switch 140 is adapted to actuate the functioning of the therapeutic device 100 and the communication port 150 is adapted to enable the connection of the therapeutic device 100 with at least one external electronic communication device enabled with at least one wireless communication technology which may be either Bluetooth, or Wireless-Fidelity (Wi-Fi), or Near Field Communication (NFC) or ZigBee, or Z-Wave, or an Internet Protocol (IP) version 6 Low-power Wireless Personal Area Network (6LoWPAN).

Figure 2:
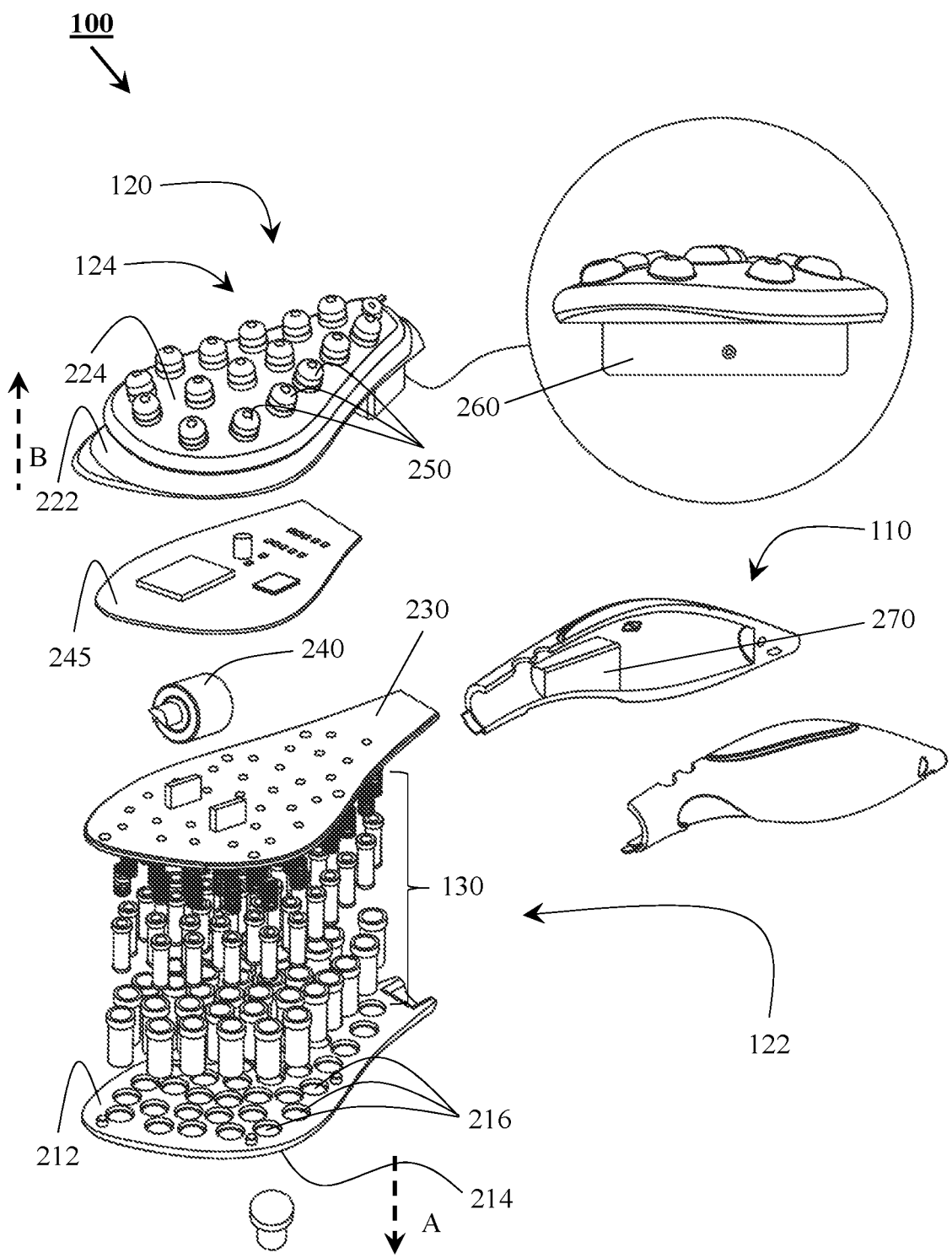
FIG. 2 illustrates an exploded view of the therapeutic device of FIG. 1.

FIG. 2 illustrates an exploded view of the therapeutic device 100 of FIG. 1. As illustrated in FIG. 2, the first functional module 122 includes a first plate 212. The first plate 212 has a first surface 214 that is oriented, downwards as per the illustrated configuration, in a direction represented by the letter 'A'. Additionally, the first plate 212 includes a plurality of first openings 216 in form of through-holes or slots or punches of predefined shapes. The second functional module 124 includes a second plate 222. The second plate 222 includes a second surface 224 that is oriented, upwards as per the illustrated configuration, in a direction represented by the letter 'B'. However, the therapeutic device 100 may be held in any configuration, the second surface 224 would always be oriented in the opposite direction to the first surface 214. The second surface 224 also includes a plurality of secondary LEDs 250 that are oriented in the direction of the orientation of the second surface 224.

In accordance with several alternate embodiments of the invention, the plurality of primary LEDs 132 may be arranged in the first plate 212 of the first functional module 122 of the functional unit 120 of the therapeutic device 100 using preferably chip-on-board (CoB) technology. The chip-on-board (CoB) arrangement of the plurality of primary LEDs 132 and the plurality of secondary LEDs 250 facilitate the advantages of compactness due to small size of the Light Emitting Diode (LED) chip, the high intensity at close distances, high uniformity at close working distances and best thermal performance with better lifetime, stability, and reliability. The plurality of secondary LEDs 250 may also be arranged using the aforementioned Chip-on-Board (CoB) technology in the second plate 222 of the second functional module 124 of the functional unit 120 of the therapeutic device 100. Further, in several embodiments, the diameter of each one of the plurality of secondary LEDs 250 is larger than the diameter of each one of the plurality of primary LEDs 132. It is further envisaged that the plurality of primary LEDs 132 and the plurality of secondary LEDs 250 that are used in the therapeutic device 100 are either infrared (IR) LEDs, or red LEDs, or any combination thereof.

The functional unit 120 further includes an intermediary plate 230 located between the first plate 212 and the second plate 222. The plurality of teeth 130 as illustrated above are installed onto the intermediary plate 230 and are made to protrude through the plurality of respective first openings 216. There is also provided a vibration motor 240 mounted on the intermediary plate 230. The vibration motor 240 is configured to generate vibrations with predetermined vibration characteristics, such as amplitude and frequency of the vibrations. The vibration characteristics may be altered in correlation with potential difference applied across terminals of the vibration motor 240 to achieve a predesigned or preconfigured massaging effect on the body of the user. The vibration motor 240 may, although not bindingly, either be an eccentric rotating mass (ERM) vibration motor or a linear resonant actuator (LRA). The functioning of the vibration motor 240 is adapted to initiate vibration of both the first plate 212 and the second plate 222 of the functional unit 120 of the therapeutic device 100. The diameter of the vibration motor 240 may be in the range of 3 mm through 9 mm with the voltage rating in the range of 1.5V through 9V. The vibration motor 240 is preferably made of pure copper wire to increase the efficiency of the vibration motor 240 which in turn increases the efficiency of the therapeutic device. The speed of the vibration motor 240 is in the range of 5000 rotation per minute (rpm) through 10000 rotation per minute (rpm).

There is also provided a sensor unit 245 configured to determine hair distribution data on a body portion of a user. It has generally been observed that the physical properties and distribution of human hair particularly scalp hair varies with ethnicity and hair color. On average, the human scalp contains between 175 and 300 hair fibers per square centimeter of the surface. If the hair is assumed to stand perpendicular to the scalp surface, the bulk porosity is in the range of 98.5%~99.5%, and the bulk density is in the range of 10 kg/m$^3$~20 kg/m$^3$. If the hair is sloped at 75° from the scalp normal, the bulk density range is increased to 40 kg/m3~80 kg/m3 with 94%~97% bulk porosity. When the hair is combed using the therapeutic device 100 with the first functional module 122 proximal to the scalp area, then the combing of the scalp area of the user in contact with the first functional module 122 generates sound waves. The sensor unit 245 is configured to analyze the generated sound waves for characteristics such as amplitude and wavelength of the generated sound waves. The analysis of the sound waves provides an estimated quantitative value of the density and volume of the hairs of the scalp in contact with the first functional module 122. Based on these values of density and volume of the hairs of the exposed area of the scalp, the required therapeutic response in the form of light therapy using the light emitted from the plurality of primary LEDs 132 is effectuated.

The gripping unit 110, the functional unit 120, the first plate 212, the second plate 222 and the intermediary plate 230 of the therapeutic device 100 are preferably made of a thermoplastic material such as Low-Density Polyethylene (LDPE), High-Density Polyethylene (HDPE), Poly Vinyl Chloride (PVC), Polypropylene (PP), and polystyrene, etc. Also illustrated in FIG. 2 the therapeutic device 100 includes a reservoir 260 provided in the functional unit 120. The reservoir 260 is adapted to store serum for facilitating hair growth and repairing damaged hair. In the context of this specification, the term "serum" is envisaged to include all the substances such as shampoos, conditioners, serums, hair sprays, waxes, gels, and mousses, etc. that act on endocuticles and exocuticles of the hair for promoting aesthetics, strength, length, and overall health of human hair. More information on such substances and their applications can be found in the article cited as Madnani N, Khan K. *Hair cosmetics. Indian J Dermatol Venereol Leprol* 2013; 79:654-67 that is included herein in its entirety, by reference. Also, FIG. 2 illustrates a control module 270 which includes control circuitry and the control architecture of the therapeutic device 100. The functioning of the control module 270 would be discussed in detail in a later discussion.

Figure 3A:
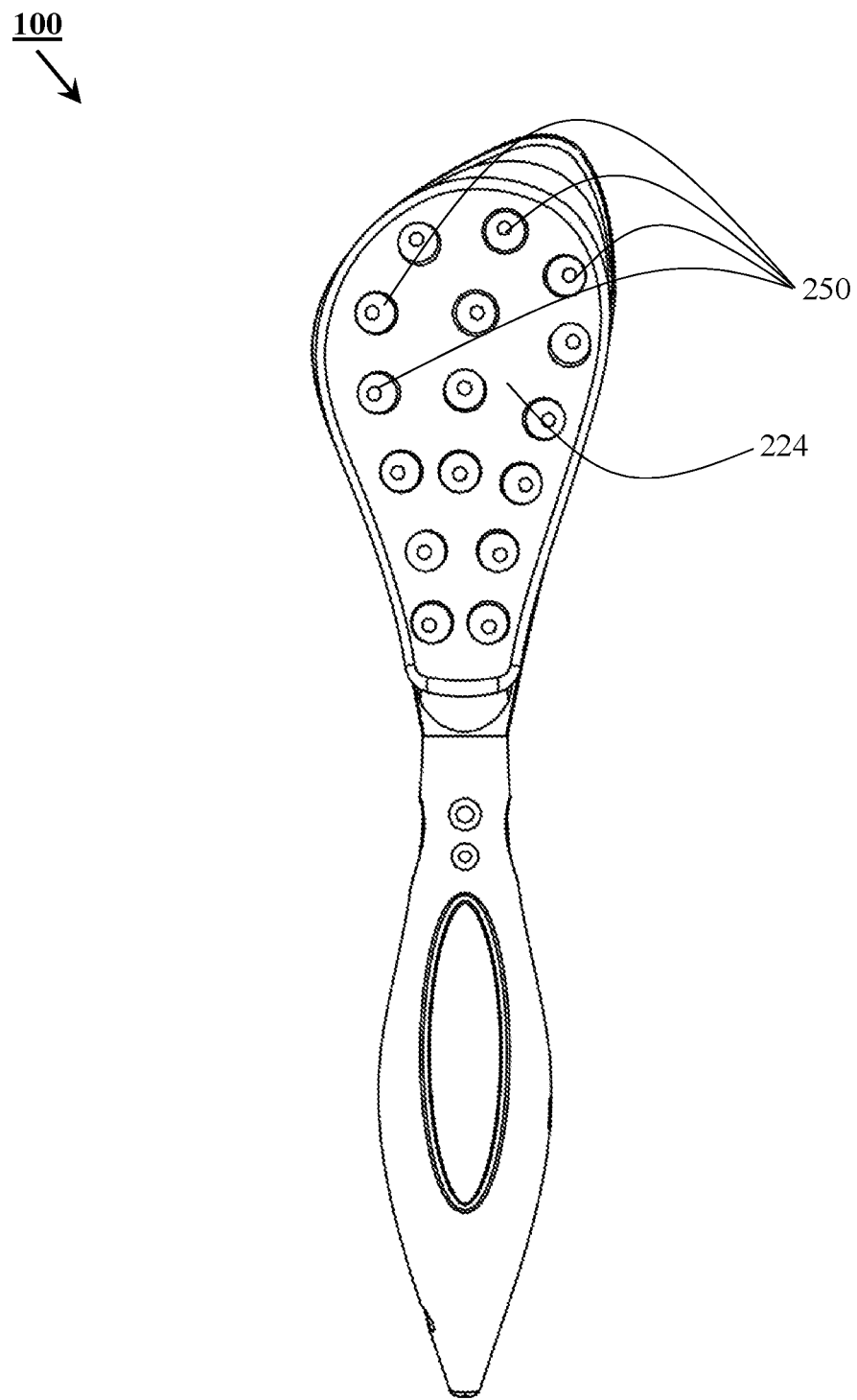
FIG. 3A illustrates a top view of the therapeutic device of FIG. 1.
Figure 3B:
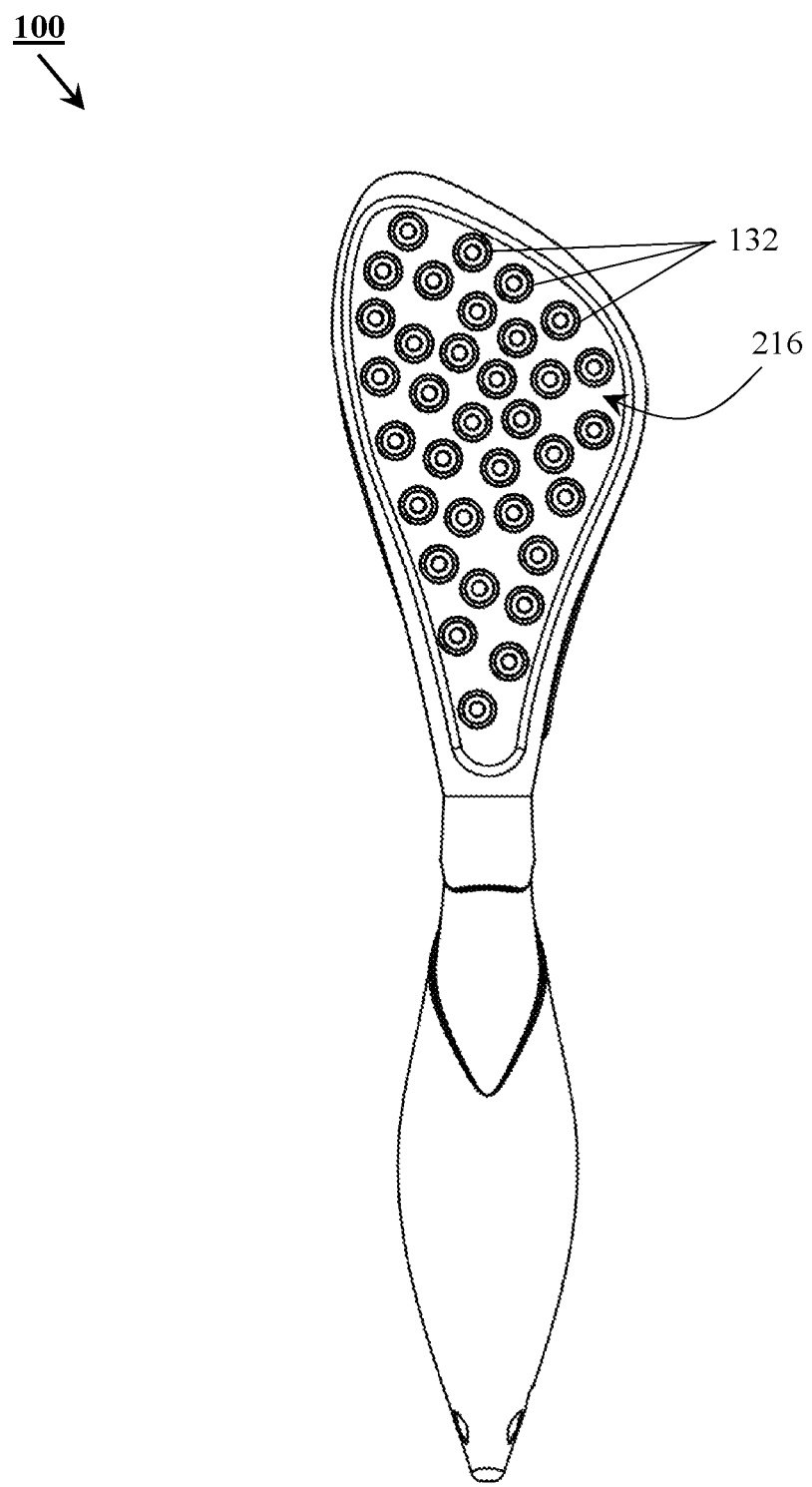
FIG. 3B illustrates a bottom view of the therapeutic device of FIG. 1.

FIG. 3A illustrates a top view of the therapeutic device 100 of FIG. 1. As illustrated, the plurality of secondary LEDs 250 is located on the second surface 224 to facilitate light therapy, massage therapy, and skincare. FIG. 3B illustrates a bottom view of the therapeutic device 100 of FIG. 1, including the plurality of primary LEDs 132 that is adapted to protrude through the plurality of respective first openings 216. Furthermore, the plurality of primary LEDs 132 is adapted to provide light therapy, massage therapy, hair care, and skincare.

Figure 3C:
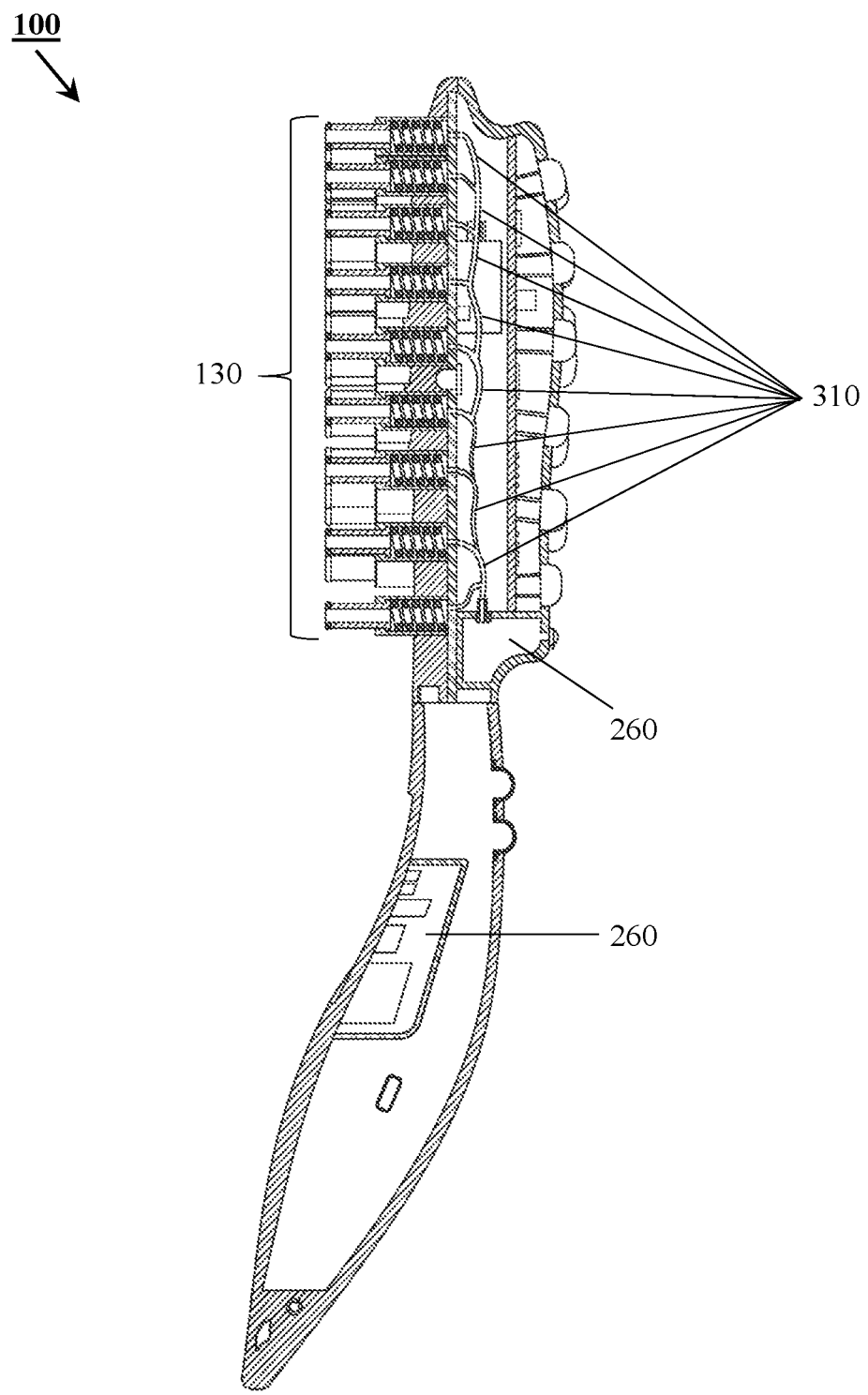
FIG. 3C illustrates a side sectional view of the therapeutic device of FIG. 1.
Figure 3D:
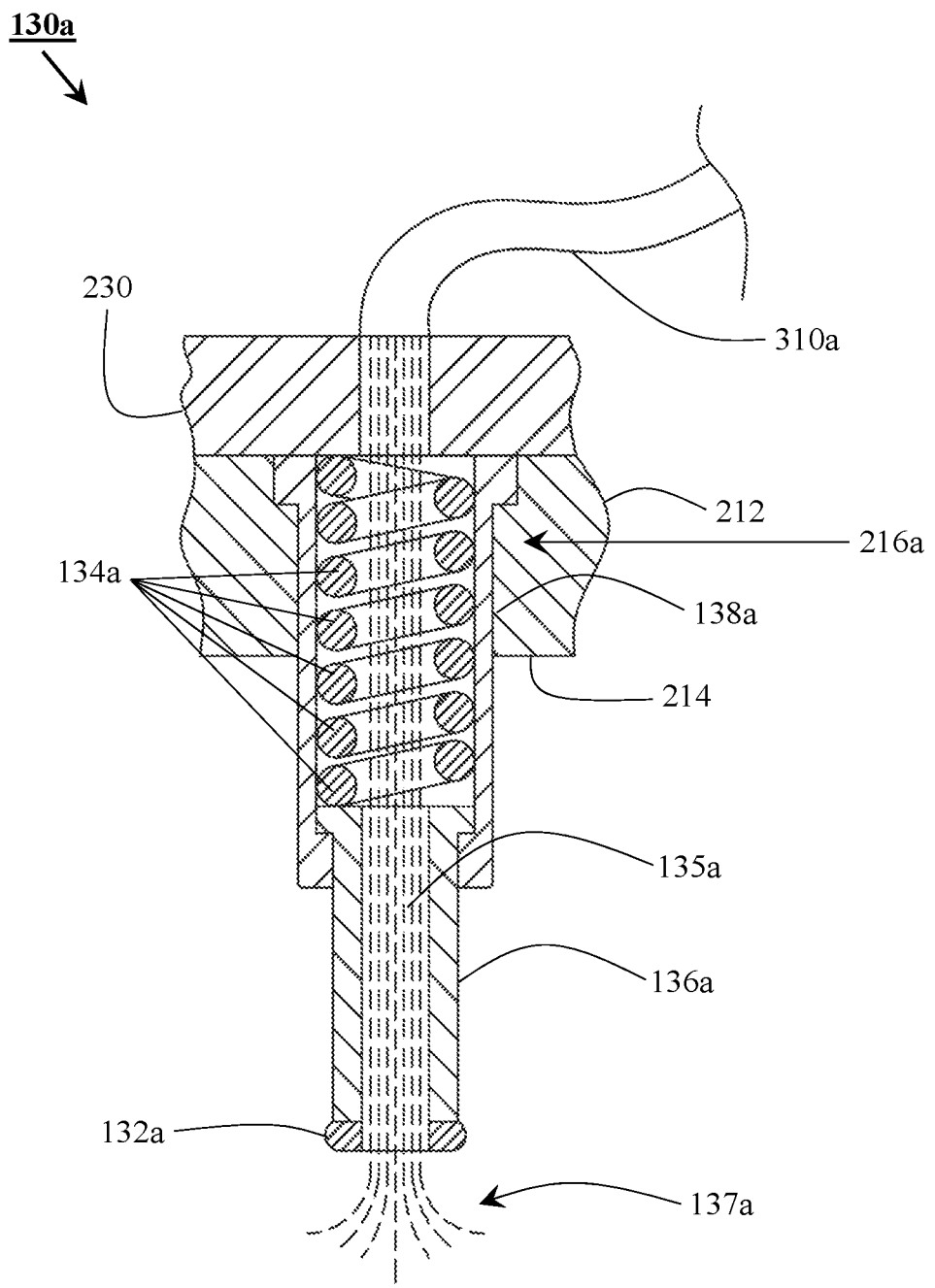
FIG. 3D illustrates a sectional view of a tooth of a plurality of teeth of the therapeutic device of FIG. 1.

FIG. 3C illustrates a side sectional view of the therapeutic device 100 of FIG. 1. As illustrated in FIG. 3C. As illustrated in FIG. 3C, a plurality of fluid channels 310 connects the reservoir 260 with the plurality of respective teeth 130. The plurality of fluid channels 310 may either be tubes or conduits of flexible polymeric material or may be generated by providing channel-shaped cavities during the molding process of the functional unit 120. Also, the plurality of teeth 130 is adapted to dispense the serum to the hair and scalp of the user, during the use of the therapeutic device 100. FIG. 3D illustrates a sectional view of a tooth 130a of the plurality of teeth 130 of the therapeutic device 100 of FIG. 1. It is illustrated in FIG. 3D that the tooth 130a includes an elastic member 134a attached with the intermediary plate 230. The elastic member 134a may in that regard be compression or a tension spring of helical construction. The elastic member 134a may also be a pad made out of an elastomeric material, such as natural rubber, neoprene, buna-n, and buna-s, etc. Also, the elastic member 134a may be a coiled film or a diaphragm made out of a metallic, polymeric, or composite material. Also, the tooth 130a includes a primary tube 136a attached with the elastic member 134a.

It is also illustrated that the primary tube 136a includes a respective primary LED 132a of the plurality of primary LEDs 132. Also, a secondary tube 138a has been coaxially provided with respect to the primary tube 136a. The secondary tube 138a has an internal diameter that is larger than an external diameter of the primary tube 136a, giving the tooth 130a a telescopic construction. It is further envisaged that the secondary tube 138a may be fixed with either one or both of a respective first opening 216a of the plurality of first openings 216 of the first plate 212, and the intermediary plate 230. In several embodiments, compression of the primary tube 136a against the elastic member 134a is configured to activate the respective primary LED 132a, during usage. A fluid channel 310a of the plurality of fluid channels 310 connects the reservoir 260 with the tooth 130a. Since both the primary tube 136a and the secondary tube 138a are hollow tubes open at both ends, the assembly of the tooth 130a creates a serum channel 135a that allows the serum 137a to be dispensed from the tooth 130a. It can also be observed that the tooth 130a is oriented in the direction of the orientation of the first surface 214, and the same would apply to all of the plurality of teeth 130.

The functional unit 120 of the therapeutic device 100 is adapted to function in at least one therapeutic mode at any given instant of time. The available therapeutic modes, in that regard, may include massage therapy and light therapy. The user is envisaged to be enabled to control the functioning of the therapeutic device 100 either automatically or manually. The automatic way of controlling the functioning of the therapeutic device 100 requires a wireless or wired communication to be initiated with an external electronic communication device associated with the user via the communication port 150. In that regard, the therapeutic device 100 is envisaged to be included with a preconfigured control architecture.

Figure 4:
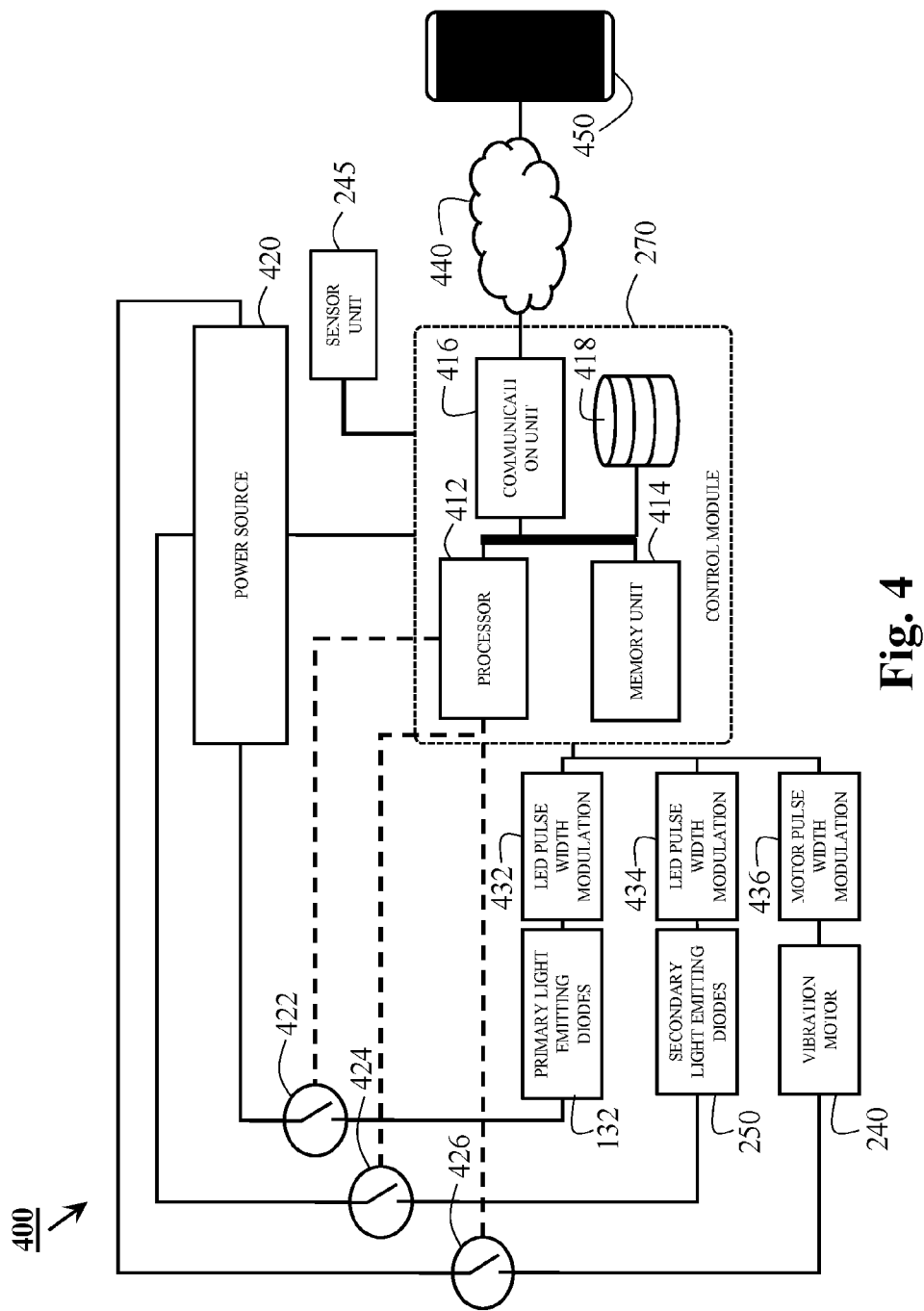
FIG. 4 illustrates a control architecture for the therapeutic device of FIG. 1, in accordance with an embodiment of the present invention.

FIG. 4 illustrates a control architecture 400 for the therapeutic device of FIG. 1, in accordance with an embodiment of the present invention. The control architecture 400 includes a control module 270. The control module 270, in turn, includes a processor 412, a memory unit 414, a communication unit 416, and a storage device 418. The processor 412 may be a general-purpose processor, a Field Programmable Gate Array (FPGA) or an Application Specific Integrated Circuit (ASIC), etc. Additionally, the memory unit 414 may be a volatile memory unit such as Static Random Access Memory (SRAM) and Dynamic Random Access Memory (DRAM) of types such as Asynchronous DRAM, Synchronous DRAM, Double Data Rate SDRAM, Rambus DRAM, and Cache DRAM, etc. The storage device 418 may be EPROM, EEPROM, or flash memory based storage device. The communication unit 416 may be able to connect to an external network 440 through wired media such as those implementing IEEE 802.3 Ethernet standard or wireless media such as those implementing Bluetooth, Near Field Communication (NFC) and 802.11 Wireless Fidelity (Wi-Fi) or combinations thereof. In that regard, the communication unit 416 may include a port such as an Ethernet port or a Universal Serial Bus (USB) port or may be provided with a radio frequency transceiver.

Electrical power to power the control architecture 400 and the plurality of primary 132 and secondary 250 LEDs, the sensor unit 245 and the vibration motor 240 may be made available through a power source 420 that may be rechargeable or replaceable batteries. The rechargeable batteries may be based on compositions such as Lithium-ion, Lithium-polymer, Nickel-metal-hydride, and any other technology that may be released in foreseeable future. The power delivery to the plurality of primary 132 and secondary 250 LEDs and the vibration motor 240 may be controlled by the processor 412 through control switches 422, 424, and 426, respectively. The control switches 422, 424, and 426 may be electromechanical control switches such as relays or maybe solid-state switches such as transistors. An external electronic communication device 450 is connected with the therapeutic device 100 through the external network 440 and the communication unit 416. The external electronic communication device 450 associated with the user is either a cell phone, or a lap-top computer, or a tablet computer, or a notebook computer, or an iPhone, or an iPod, or an iPad.

It is further envisaged that emission characteristics of the plurality of primary LEDs 132 and the plurality of secondary LEDs 250 be reconfigurable. The emission characteristics of the plurality of primary 132 and the secondary 250 LEDs include luminous flux, luminous intensity, power consumption, frequency, wavelength, mode of operation (pulsed or continuous). The processor 412 is capable of achieving the reconfiguration of the plurality of primary 132 and the secondary 250 LEDs through the control switches 422 and 424, respectively and through LED pulse width modulation units 432 and 434. Also, the processor 412 may be able to control the vibration characteristics of the vibration motor 240 using a motor pulse width modulation unit 436.

Figure 5:
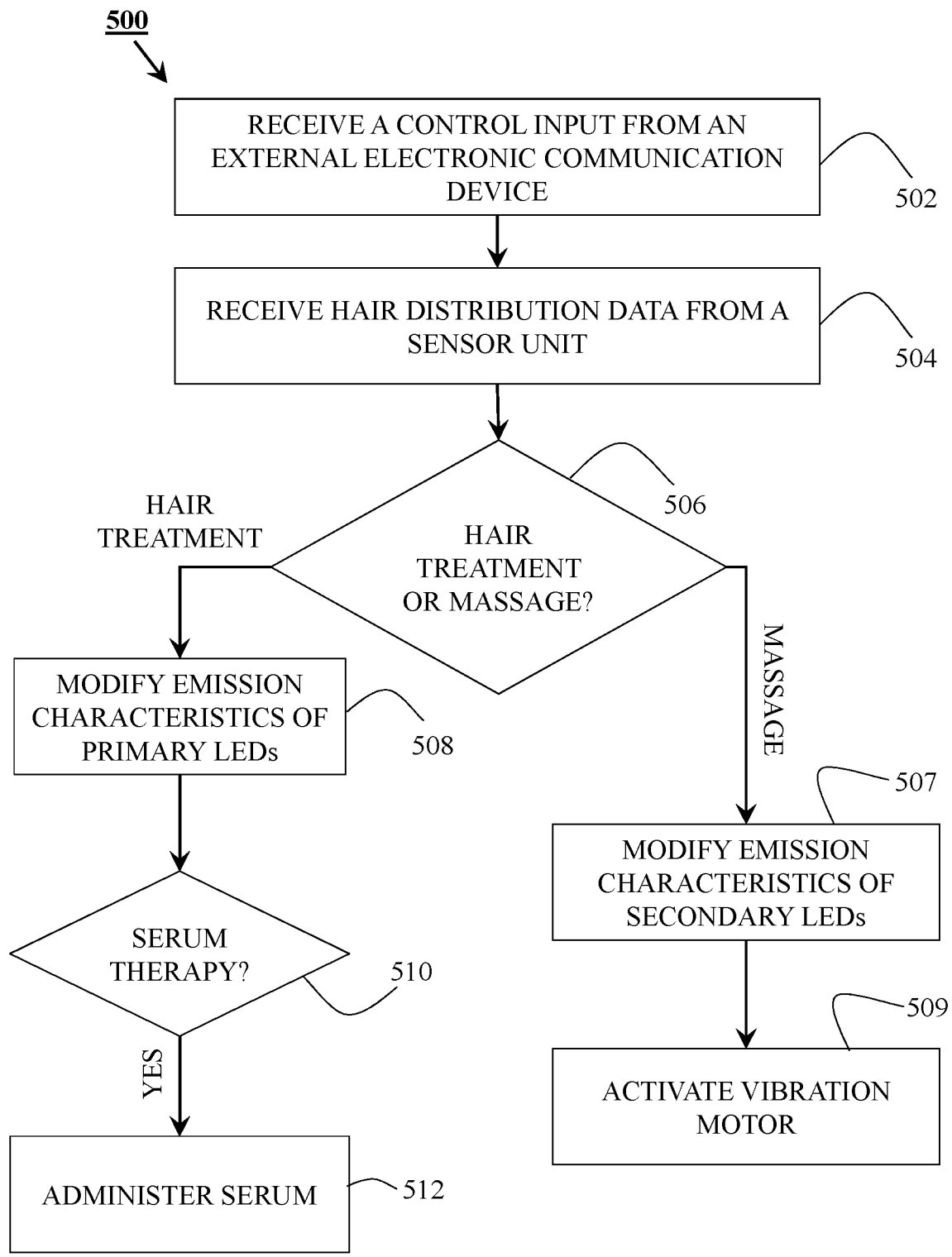
FIG. 5 illustrates a method for operating the therapeutic device of FIG. 1, in accordance with an embodiment of the present invention.

FIG. 5 illustrates a method 500 for operating the therapeutic device 100 of FIG. 1, in accordance with an embodiment of the present invention. The method 500 begins at step 502 when a control input is received by the processor 412, from the external electronic communication device 450 through the external network 440. At step 504, the processor 412 receives the hair distribution data from the sensor unit 245. At step 506, the processor 412 determines from the control input, if the therapeutic device 100 is going to be used as a hair treatment or a massaging apparatus. If the therapeutic device 100 is going to be used as a hair treatment apparatus, then the method 500 moves to step 508. At step 508, as the user applies the plurality of teeth 130 to their hair or scalp, the plurality of respective primary tubes 136 are compressed against the plurality of respective elastic members 134, causing the plurality of primary LEDs 132 to get activated. The processor 412, in turn, modifies the aforementioned emission characteristics of the plurality of primary LEDs 132 in correlation with one or both of the control input and the hair distribution data. At step 510, the processor 412 determines from the control input, if the serum has to be administered to the hair and scalp of the user. If the control input indicated administration of the serum, then at step 512, the processor 412 activates the plurality of fluid channels 310 through electronically controlled valves and an optional pump assembly, in order for the serum to be dispensed from the plurality of teeth 130.

Alternately, if at step 506, the processor 412 determines from the control input, the therapeutic device 100 is going to be used as massaging apparatus, the method 500 moves to step 507, where the plurality of secondary LEDs 250 is activated. In addition, the processor 412 modifies the emission characteristics of the plurality of secondary LEDs 250 in correlation with one or more of the hair distribution data and the control input. Also, at step 509, processor 412 activates the vibration motor 240 and modifies the vibration characteristics of the vibration motor 240, in order to provide massage therapy to the scalp and hair of the user.

Figure 6A:
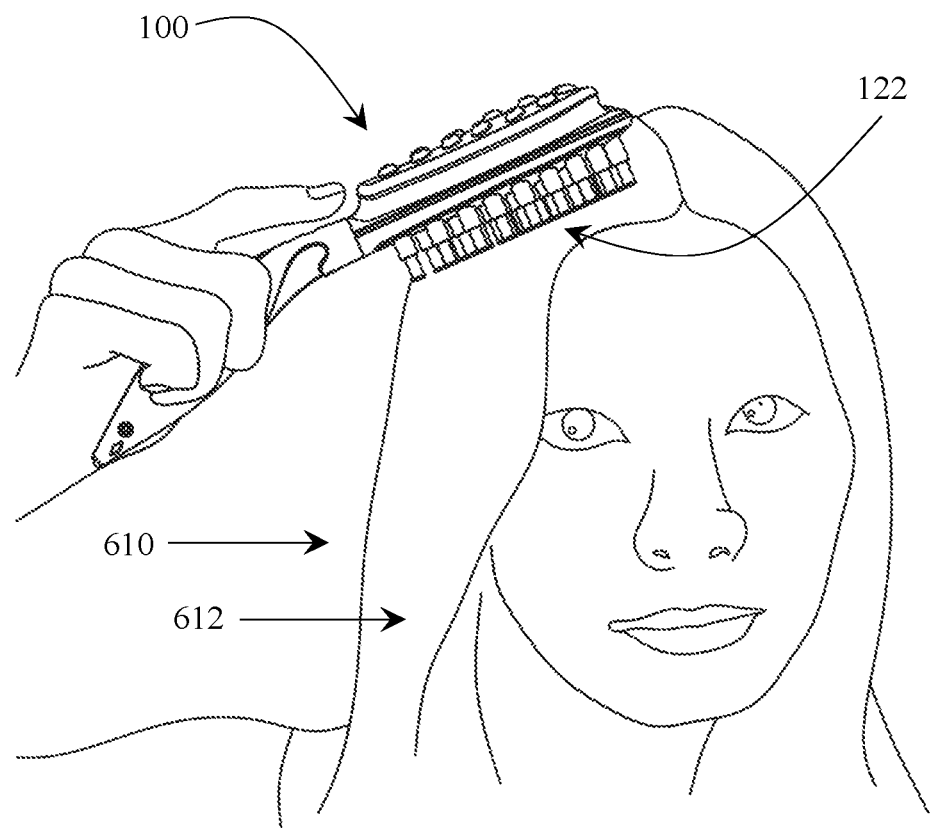
FIG. 6A illustrates a pictorial representation of the utilization of the therapeutic device as a hair treatment apparatus, in accordance with an embodiment of the present invention.
Figure 6B:
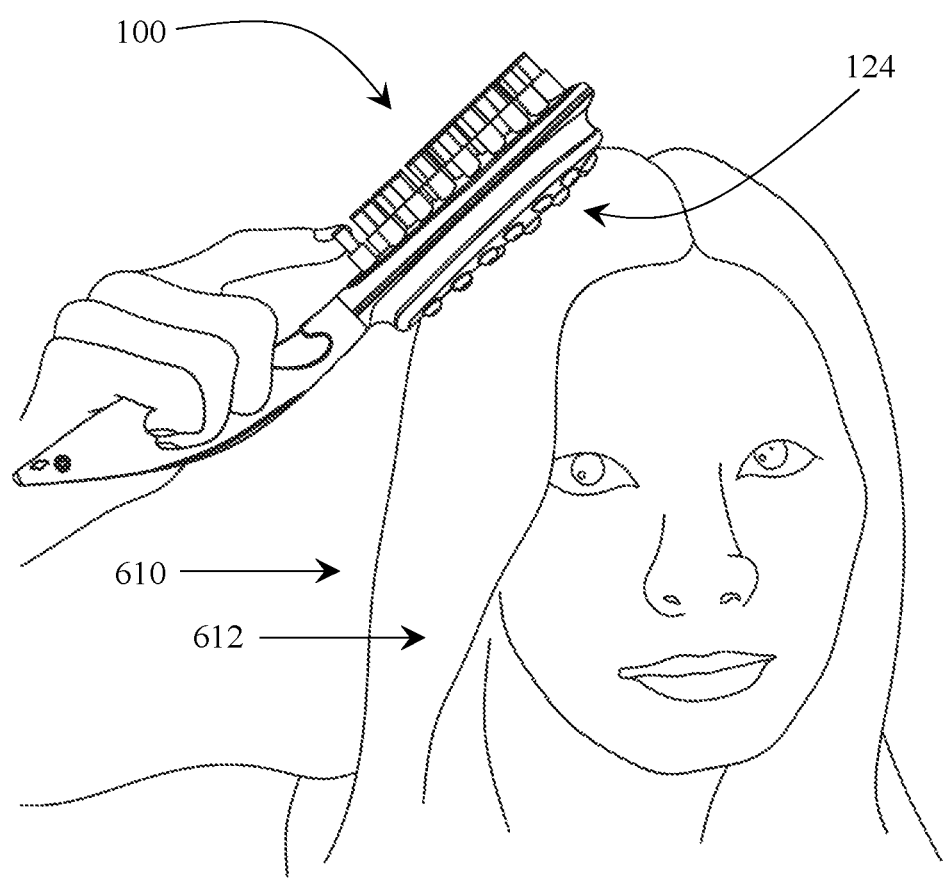
FIG. 6B illustrates a pictorial representation of the utilization of the therapeutic device as a massaging apparatus, in accordance with an embodiment of the present invention.

FIG. 6A illustrates a pictorial representation of the utilization of the therapeutic device 100 as a hair treatment apparatus, in accordance with an embodiment of the present invention. In the illustrative drawing of FIG. 6A, a person 610 is shown using the therapeutic device 100. The person 610 firmly holds the therapeutic device 100 using the gripping unit 110. The first functional module 122 of the therapeutic device 100 is in proximity to the hair 612 of the person 610. FIG. 6B illustrates a pictorial representation of the utilization of the therapeutic device 100 as a massaging apparatus, in accordance with an embodiment of the present invention. The person 610 firmly holds the therapeutic device 100 using the gripping unit 110. The second functional module 124 of the therapeutic device 100 is in proximity to the hairs 612.

The present invention provides a light-based therapeutic device cost-effective therapeutic device configured in the form of a hair comb for non-invasive massage therapy and the treatment of hair loss and stimulation of hair growth in an individual by providing at least one of massage therapy and light therapy to a targeted area in the body of a user based on his/her requirement, the targeted area being scalp, hair and body skin surface. The light-based therapeutic device disclosed in the present invention is a reliable and easily operable therapeutic device with reduced side effects and reduced treatment time. The therapeutic device disclosed in the present invention exhibits long-term safety and provides effective massage therapy and for the treatment of hair loss and stimulation of hair growth in an individual irrespective of his or her gender, age, and geography. The therapeutic device disclosed in the present invention a light-based therapeutic device with reduced treatment time for massage therapy and for the treatment of hair loss and stimulation of hair growth in an individual.

The programming instructions can be, for example, computer-executable and/or logic implemented instructions. In some examples, a computing device is configured to provide various operations, functions, or actions in response to the programming instructions conveyed to the computing device by one or more of the computer-readable medium, the computer recordable medium, and/or the communications medium. The non-transitory computer-readable medium can also be distributed among multiple data storage elements, which could be remotely located from each other. The computing device that executes some or all of the stored instructions can be a micro-fabrication controller or another computing platform. Alternatively, the computing device that executes some or all of the stored instructions could be remotely located computer systems, such as a server.

Further, while one or more operations have been described as being performed by or otherwise related to certain modules, devices or entities, the operations may be performed by or otherwise related to any module, device or entity. As such, any function or operation that has been described as being performed by a module could alternatively be performed by a different server, by the cloud computing platform, or a combination thereof. Further, the operations need not be performed in the disclosed order, although in some examples, an order may be preferred. Also, not all functions need to be performed to achieve the desired advantages of the disclosed system and method, and therefore not all functions are required.

Various modifications to these embodiments are apparent to those skilled in the art, from the description and the accompanying drawings. The principles associated with the various embodiments described herein may be applied to other embodiments. Therefore, the description is not intended to be limited to the embodiments shown along with the accompanying drawings but is to be providing broadest scope of consistent with the principles and the novel and inventive features disclosed or suggested herein. Accordingly, the invention is anticipated to hold on to all other such alternatives, modifications, and variations that fall within the scope of the present invention and appended claims.

The invention claimed is:

1. A therapeutic device for human hair and skincare, the therapeutic device comprising:
   a gripping unit;
   a functional unit including a first functional module and a second functional module, the first functional module including a first plate and a second functional module including a second plate, wherein a second surface of the second plate is oriented in an opposite direction to a first surface of the first plate;
   a plurality of teeth oriented in the direction of the orientation of the first surface, the plurality of teeth including a plurality of respective primary Light Emitting Diodes (LEDs);
   a plurality of secondary LEDs provided on the second plate and oriented in the direction of the orientation of the second surface; and
   a sensor unit configured to determine hair distribution data on a body portion of a user
   wherein the functional unit further comprises an intermediary plate located between the first plate and the second plate, wherein the first plate includes a plurality of first openings, the plurality of teeth being installed onto the intermediary plate and being adapted to protrude through the plurality of first openings;
   wherein each tooth of the plurality of teeth includes:
      an elastic member attached with the intermediary plate,
      a primary tube attached with the elastic member, the primary tube including a respective primary LED of the plurality of primary LEDs, and
      a secondary tube coaxially provided with respect to the primary tube and having an internal diameter that is larger than an external diameter of the primary tube, the secondary tube being fixed to one or both of a respective first opening of the plurality of first openings, and the intermediary plate.

2. The therapeutic device as claimed in claim 1, wherein emission characteristics of the plurality of primary LEDs and the plurality of secondary LEDs are reconfigurable.

3. The therapeutic device as claimed in claim 1, wherein the plurality of primary LEDs and the plurality of secondary LEDs are configured to emit electromagnetic radiation in red frequency ranges, infrared frequency ranges, and combinations thereof.

4. The therapeutic device as claimed in claim 1, wherein diameters of the plurality of secondary LEDs is greater than diameters of the plurality of primary LEDs.

5. The therapeutic device as claimed in claim 1, wherein the functional unit further includes a reservoir adapted to store a serum, and a plurality of fluid channels connecting the reservoir with the plurality of respective teeth, the plurality of teeth being adapted to dispense the serum.

6. The therapeutic device as claimed in claim 1, further comprising a vibration motor configured to generate vibrations with predetermined vibration characteristics, the vibration motor being located between the first plate and the second plate.

7. The therapeutic device as claimed in claim 6, further comprising an intermediary plate located between the first plate and the second plate, wherein the vibration motor is installed with the intermediary plate.

8. The therapeutic device as claimed in claim 1, further comprising a control unit, the control unit including a processor, a memory unit and a communication unit, the memory unit including machine-readable instructions that when executed by the processor, enable the processor to:
   receive a control input, via the communication unit, from an external electronic communication device;
   receive the hair distribution data from the sensor unit; and
   modify emission characteristics of one or both of the plurality of primary LEDs and the plurality of secondary LEDs, in correlation with one or both of the control input and the hair distribution data.

9. The therapeutic device as claimed in claim 1, wherein compression of the primary tube against the elastic member is configured to activate the respective primary LED.

10. The therapeutic device as claimed in claim 1, wherein the plurality of primary LEDs are provided within the plurality of respective teeth and the plurality of secondary LEDs are provided on the second surface through Chip-on-Board (CoB) technology.

11. A therapeutic device for human hair and skincare, the therapeutic device comprising:
   a gripping unit;
   a functional unit including a first functional module and a second functional module, the first functional module including a first plate and a second functional module including a second plate, wherein a second surface of the second plate is oriented in an opposite direction to a first surface of the first plate;
   an intermediary plate located between the first plate and the second plate;
   a vibration motor configured to generate vibrations with predetermined vibration characteristics;
   a plurality of teeth oriented in the direction of the orientation of the first surface, the plurality of teeth including a plurality of respective primary Light Emitting Diodes (LEDs);
   a plurality of secondary LEDs provided on the second plate and oriented in the direction of the orientation of the second surface; and
   a sensor unit adapted to determine hair distribution data on a body portion of a user;
   wherein the first plate includes a plurality of first openings, the plurality of teeth being installed onto the intermediary plate and being adapted to protrude through the plurality of first openings;
wherein each tooth of the plurality of teeth includes:
an elastic member attached with the intermediary plate,
a primary tube attached with the elastic member, the primary tube including a respective primary LED of the plurality of primary LEDs, and
a secondary tube coaxially provided with respect to the primary tube and having an internal diameter that is larger than an external diameter of the primary tube, the secondary tube being fixed to one or both of a respective first opening of the plurality of first openings and the intermediary plate.

12. The therapeutic device as claimed in claim 11, further comprising a control unit, the control unit including a processor, a memory unit and a communication unit, the memory unit including machine-readable instructions that when executed by the processor, enable the processor to:
receive a control input, via the communication unit, from an external electronic communication device;
receive the hair distribution data from the sensor unit;
modify emission characteristics of the plurality of primary LEDs and the plurality of secondary LEDs, in correlation with one or both of the control input and the hair distribution data; and
activate the vibration motor in correlation with the control input.

\* \* \* \* \*